(12) United States Patent
Chen et al.

(10) Patent No.: US 12,399,067 B2
(45) Date of Patent: Aug. 26, 2025

(54) APPARATUS, SYSTEM, AND METHOD FOR MEASURING THE TEMPERATURE OF A SUBSTRATE

(71) Applicant: Taiwan Semiconductor Manufacturing Co., Ltd., Hsinchu (TW)

(72) Inventors: Tz-Shian Chen, Hsinchu (TW); Yi-Chao Wang, Hsinchu (TW); Wen-Yen Chen, Hsinchu (TW); Li-Ting Wang, Hsinchu (TW); Huicheng Chang, Hsinchu (TW); Yee-Chia Yeo, Hsinchu (TW)

(73) Assignee: Taiwan Semiconductor Manufacturing Co., Ltd., Hsinchu (TW)

( * ) Notice: Subject to any disclaimer, the term of this patent is extended or adjusted under 35 U.S.C. 154(b) by 807 days.

(21) Appl. No.: 17/461,688

(22) Filed: Aug. 30, 2021

(65) Prior Publication Data
US 2023/0060543 A1    Mar. 2, 2023

(51) Int. Cl.
*G01K 11/125* (2021.01)
*H01L 21/66* (2006.01)
*H01L 21/67* (2006.01)

(52) U.S. Cl.
CPC ...... *G01K 11/125* (2013.01); *H01L 21/67248* (2013.01); *H01L 22/12* (2013.01)

(58) Field of Classification Search
None
See application file for complete search history.

(56) References Cited

U.S. PATENT DOCUMENTS

| | | | |
|---|---|---|---|
| 2006/0215165 A1* | 9/2006 | Melman | G01N 21/553 356/445 |
| 2007/0119815 A1* | 5/2007 | Zhang | H01L 29/66757 216/65 |
| 2008/0081298 A1* | 4/2008 | Tanaka | G03F 7/70383 430/327 |

* cited by examiner

*Primary Examiner* — Erica S Lin
(74) *Attorney, Agent, or Firm* — Seed Intellectual Property Law Group LLP

(57) ABSTRACT

A temperature measuring apparatus for measuring a temperature of a substrate is described. A light emitting source that emits light signals such as laser pulses are applied to the substrate. A detector on the other side of the light emitting source receives the reflected laser pulses. The detector further receives emission signals associated with temperature or energy density that is radiated from the surface of the substrate. The temperature measuring apparatus determines the temperature of the substrate during a thermal process using the received laser pulses and the emission signals. To improve the signal to noise ratio of the reflected laser pulses, a polarizer may be used to polarize the laser pulses to have a S polarization. The angle in which the polarized laser pulses are applied towards the substrate may also be controlled to enhance the signal to noise ratio at the detector's end.

20 Claims, 14 Drawing Sheets

APPARATUS, SYSTEM, AND METHOD FOR MEASURING THE TEMPERATURE OF A SUBSTRATE

BACKGROUND

Various methods and approaches may be used in monitoring the anneal process during a semiconductor manufacturing process. One approach of monitoring the anneal process includes using a time resolved reflectivity TRR method. However, such method is not effective in detecting the slight variations that occur during this process. Such shortcomings of the time resolved reflectivity method may lead to a degraded process control of the overall semiconductor manufacturing process.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1A:
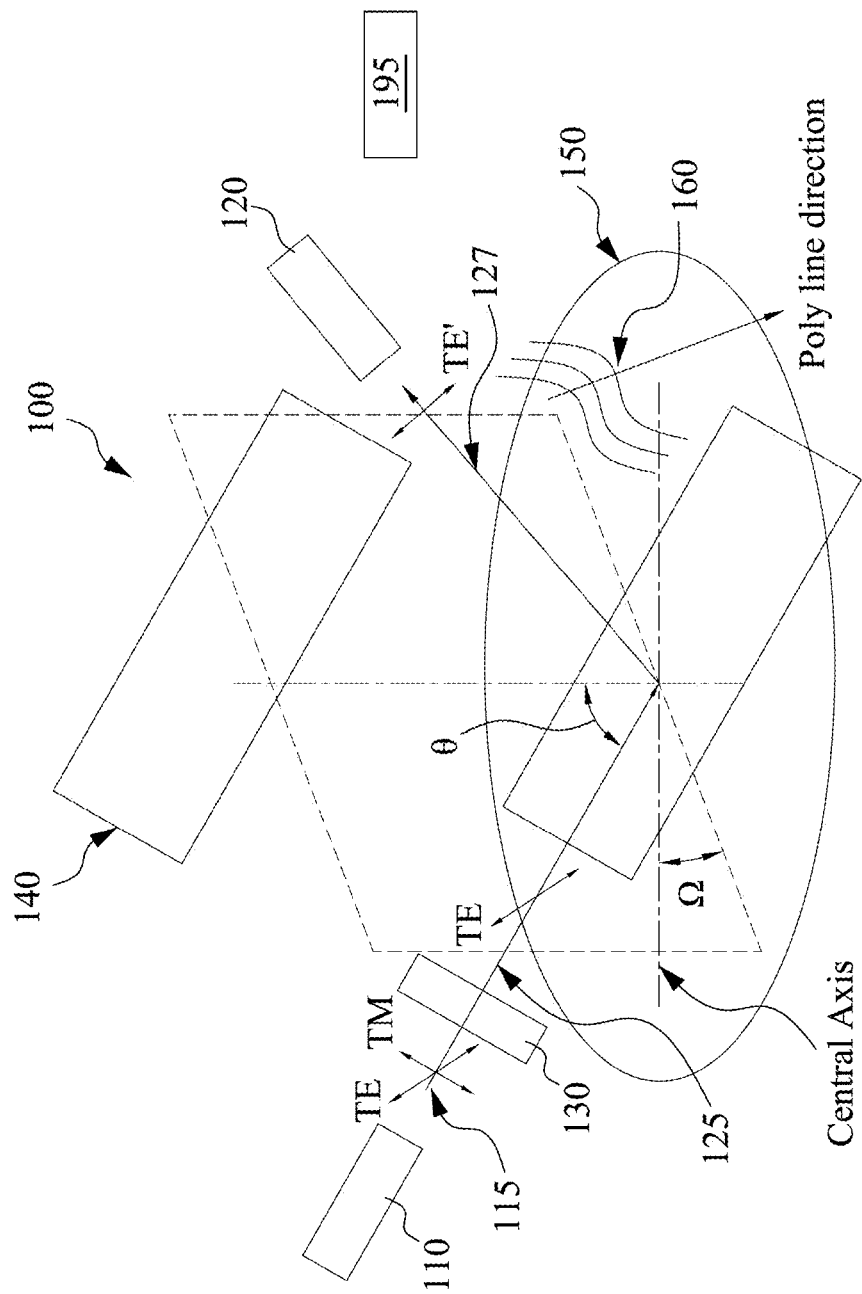
FIG. 1A illustrates a schematic diagram of a temperature evaluating system for a substrate according to one or more embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Terms such as "attached," "affixed," "connected" and "interconnected," refer to a relationship wherein structures are secured or attached to one another either directly or indirectly through intervening structures, as well as both movable or rigid attachments or relationships, unless expressly described otherwise.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference will now be made in detail to the present embodiments of the disclosure, examples of which are illustrated in the accompanying drawings. Wherever possible, the same reference numbers are used in the drawings and the description to refer to the same or like parts.

The inventors of the present disclosure recognized the problems of process control worsening due to the time resolved reflectivity method for anneal monitoring in the related art. Accordingly, the inventors came up with a method of metrology that utilizes both time resolved reflectivity and time resolved emission for advanced anneal monitoring. The inventors recognized that using the combination of reflectivity signals and emission signals improves the accuracy and preciseness of determining the processing temperature.

In one or more embodiments, the present disclosure provides a novel in-situ monitor processing for sub-melt annealing and melt annealing and overcomes the short comings of the time resolved reflectivity method in the related art.

FIG. 1A illustrates a schematic diagram of a temperature evaluating system 100 for a substrate according to one or more embodiments of the present disclosure. The temperature evaluating system 100 includes a light emitting source 110, a detector 120, a polarizer 130 (or a polarized source), and a heating source 140. The light emitting source 110 generates light signals 115 such as a laser, however, the type of light signals may vary depending on the light emitting source 110. In some embodiments, the light emitting source 110 includes a probe laser. In some embodiments, the light emitting source 110 includes a diode laser. The generated light signals 115 of the light emitting source 110 include transverse magnetic (TM) waves and transverse electric (TE) waves.

In operation, the light emitting source 110 emits the light signals 115 towards a surface of a substrate 150. The examples of the substrate 150 includes a silicon Si substrate, a SiGe substrate, and a SiP substrate, or the like. The subject of the temperature evaluating system or apparatus also includes metal lines having periodic patterns. For example, the temperature evaluating system or apparatus according to the present disclosure not only detects the temperature of surfaces of the aforementioned Si substrates, SiGe substrates, SiP substrates, but also the periodic metal line patterns formed on these Si substrates, SiGe substrates, SiP substrates. When the light signals 115 reach the surface of the substrate 150, the light signals 115 are reflected off of the surface and the reflected portion of the light signals 115 is received at the detector 120.

In one or more embodiments, the polarizer 130 is positioned adjacent to the light emitting source 110. That is, the polarizer 130 is arranged in a way so the light from the light emitting source 110 passes through the polarizer 130 before it reaches the surface of the substrate 150. In some embodiments, the polarizer 130 may be implemented within the light emitting source 110 and form a unitary component. The polarizer 130 is configured to polarize the light signals 115 emitted from the light emitting source 110. In some embodiments, the polarizer 130 may be further configured to polarize the light signals 115 so that the polarized light signals 125 include the transverse electric waves. Here, the polarizer 130 may reduce or eliminate the transverse magnetic waves from the light signals 115 after polarization. The polarizer 130 improves the signal to noise ratio of the signals received at the detector's end. The features of the polarizer 130 will be further detailed below.

The polarized light signals 125 including the transverse electric waves are propagated towards the substrate 150 at a first angle θ (i.e., incident angle) and a second angle (i.e., angle between a polarization direction and a central axis of the substrate). The detector 120 is configured to receive the reflected polarized light signals 127 (e.g., time resolved reflectivity signals) from the surface of the substrate 150. Further, the detector 120 is configured to receive emission signals 160 associated with at least one of a temperature or energy density of a surface of the substrate 150. For example, when the heating source 140 (e.g., laser) is applied to the substrate 150 during, for example, an anneal process (uses the laser to anneal the substrate), the substrate 150 after being heated, radiates emission signals 160 associated with the heat.

For example, when the surface of the substrate 150 increases in temperature, emission signals 160 emitted from the substrate 150 increase (e.g., at a high temperature, high emission signals are emitted). Also, when the substrate 150 increases in temperature, the energy density of the substrate 150 increases, which in turn increases the radiation of emission signals 160. The detector 120 is configured to receive the emission signals 160 produced from the surface of the substrate 150. In some embodiments, the emission signals 160 may detected based on intensity, density, wavelength, frequency, or some other suitable parameters. For example, when the substrate shows high temperature, the emission signals 160 may have high energy density. However, other parameters may be used to measure the intensity of the emission signals. In some embodiments, the emission signals 160 may include, but are not limited to, infrared signals.

As described, adding the polarizer 130 to the light emitting source 110 improves the reflectivity signal as the polarizer 130, for example, passes mostly or only TE signals (or waves). Further, the angle in which the light signals 115 are applied to the substrate may be adjusted. Adjusting the first angle θ and the second angle Ω may produce light signals 115 having different polarization. For example, by controlling the first angle θ and the second angle Ω, it is possible to obtain a 100% S-polarization or a 90% S-polarization and 10% P-polarization. By adjusting the angles, the detector 120 may receive better signal to noise ratio.

In some embodiments, the wavelength applied by the heating source 140 ranges between about 300 nm to 320 nm. The wavelength applied by the light emitting source 110 ranges between about 600 nm to 650 nm. The range of wavelengths used by the detector 120 to receive emission signals 160 and reflectivity signals 127 is between about 1500 nm to 1600 nm. The range of the wavelengths of the emissions signals 160 are broader than that of the reflectivity signals 127 in order to detect more emission signals 160 at the detector 120. For example, bandwidth for the emission signals 160 are broader than that of the wavelength used in the light emitting source 110. As explained, with broader range of wavelengths, the detector 120 is capable of collecting more signals.

In some embodiments, the detector 120 may be implemented using any one of InGaAs, InSb, InAs, PbS, or the like. For example, InGaAs may be used to detect signals having wavelengths about 1500 nm, and InSb may be used to detect signals having wavelengths about 900 nm, and so forth. Various different materials may be used to detect emission signals with various wavelengths. These examples are not exhaustive and a person of ordinary skill in the art would understand that other suitable materials may be utilized for detecting emission signals 160 and the reflected polarized light signals 127 (e.g., time resolved reflectivity signals). The detector 120 can monitor the change of the reflectivity at various points of the substrate 150 to monitor the temperature of the surface of the substrate 150 in accordance with some embodiments of the present disclosure.

In some embodiments, the heating source 140 may include a laser, a flash lamp, a lamp (with a bulb), or the like. In the anneal monitoring process of some embodiments of the present disclosure, any one of a laser, a flash lamp, a lamp with a bulb may be used as the anneal energy source.

The temperature evaluating system 100 may evaluate a temperature of the surface of the substrate 150 using the combination of the reflected polarized light signals 127 and the emission signals 160 from the substrate 150. The emission signals 160 are independent from the reflected polarized light signals 127 (or the reflectivity signals R). In addition, the emission signals 160 are synchronized with the reflectivity signals 127. The benefit of synchronizing the emission signals 160 and the reflectivity signals 127 is that it produces a more precise temperature calculation. Moreover, synchronizing the two signals results in simplifying the temperature calculation process.

In one or more embodiments, the temperature evaluating system 100 evaluates the temperature of the surface of the substrate 150 by calculating the temperature of the surface of the substrate based on the following equation:

$$T = \frac{A}{\ln\left(1 + B \cdot \frac{\varepsilon}{TRE}\right)}$$

Here, T is the temperature of the substrate 150, A and B are constant parameters, E is emissivity which equals 1−R %. R is an intensity of the reflected polarized light signals 127, and TRE is an intensity of the emission signals. Constant parameter A is as follows:

$$A = \frac{h \cdot c}{\lambda K}$$

Constant parameter B is as follows:

$$B(\lambda) = \frac{2h \cdot c^2 \cdot G \cdot \tau \cdot \Delta\lambda \cdot R(\lambda)}{\lambda^5}$$

$\lambda$: center wavelength=1550E−9 m; $\Delta\lambda$: spectrum range; c: velocity of light (m·s$^{-1}$); h: Planck's constant (6.63E−34 m$^2$·kg·s$^{-1}$); K: Boltzmann constant (1.38E−23J·K$^{-1}$); R($\lambda$): spectral sensitivity of the detector/sensor; $\tau$: total optical transmission of the system; G is the etendue of the optical system (m$^2$·sr$^{-1}$).

In some embodiments, the intensity of the reflected polarized light signals 127 and the intensity of the emission signals may be measured in voltages. However, other metrics may be used to measure the intensity of the reflected polarized light signals 127 and the intensity of the emission signals. For example, if the light emitting source 110 outputs 100 W and the detector 120 detects about 18 W. It is possible to determine that the reflectivity of the substrate is about 18%. As described, other metrics may be used other than watt.

Figure 4:
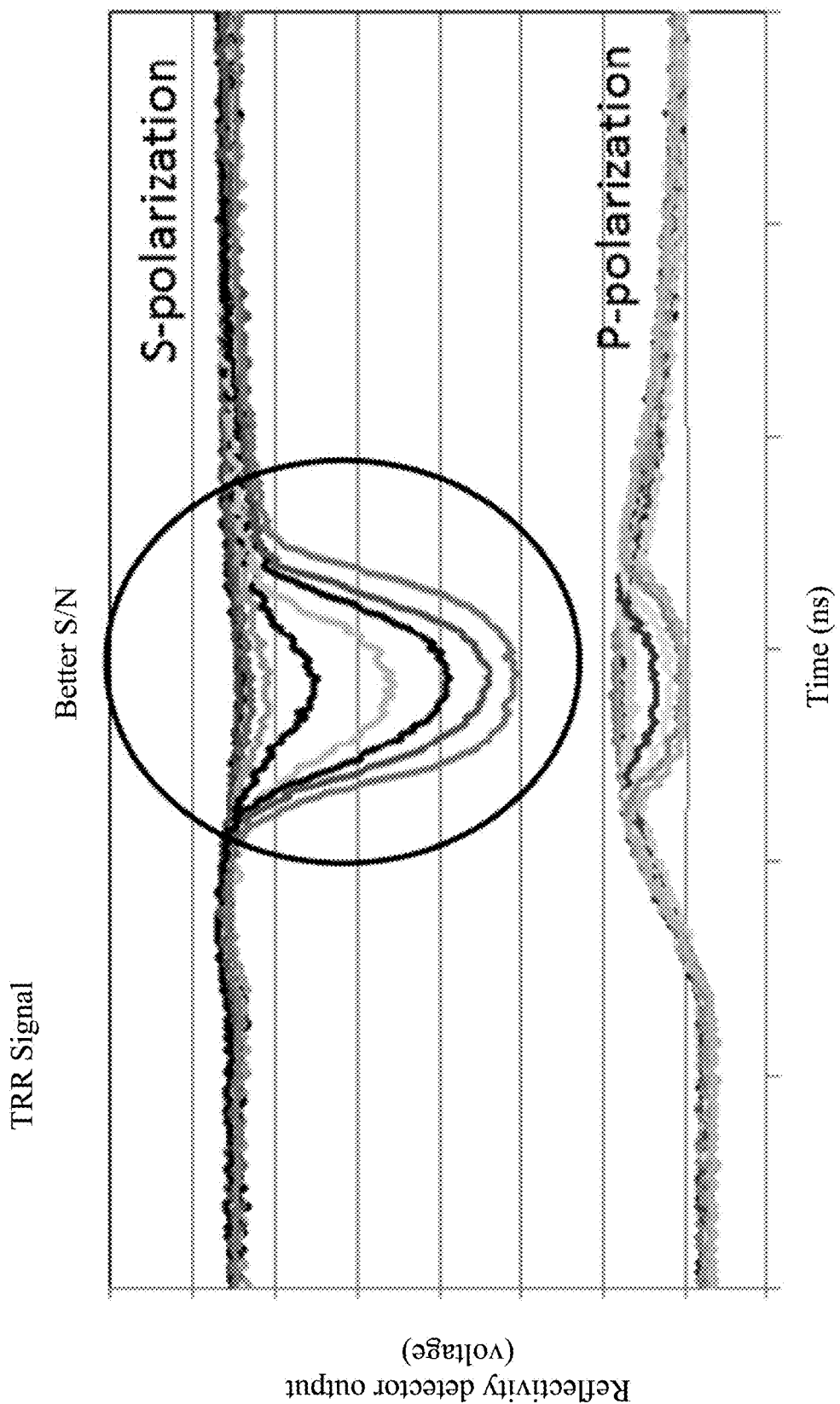
FIG. 4 illustrates a graph showing a signal to noise ratio of a time resolved reflectivity signal for TE waves and TM waves.

In some embodiments, the polarized light signals 125 are propagated toward the substrate 150 at the first angle $\theta$. The first angle $\theta$ in which the light signals 125 from the light emitting source 110 are incident on a surface of a substrate 150 or a substrate 150 can be controlled. In some embodiments, an oblique incidence angle $\theta$ is beneficial in the operation of, for example, the in situ anneal monitoring system. For example, it may be beneficial to have the first angle $\theta$ (e.g., an incidence angle) ranging from 10° to 80°. The polarized light signals 125 may be propagated toward the substrate 150 at the second angle $\Omega$ that is between about 0° to 85°. In one or more embodiments, a polarized laser incident angle is meaningful for semiconductor structures such as FINFET (fin field-effect transistor) or other periodic structures because the electric field has component along the metal wire direction or for a periodic structure, along the long axis (or the length direction) of the structure. For example, the incident electric has component along the metal grid. This means higher reflection signal for the detector 120 and better S/N ratio as shown in FIG. 4.

The temperature evaluating system or apparatus may be used not only in the laser anneal processes (at the sub melt region and the melt region) but also may be implemented in other semiconductor processes including thermal processes (e.g., thermal annealing). Further, the method of calculating the surface of the temperature T according to the above equation is independent from the anneal process itself. That is, the measurement process and the anneal process can be independent which is also another benefit of some embodiments of the present disclosure.

Figure 1B:
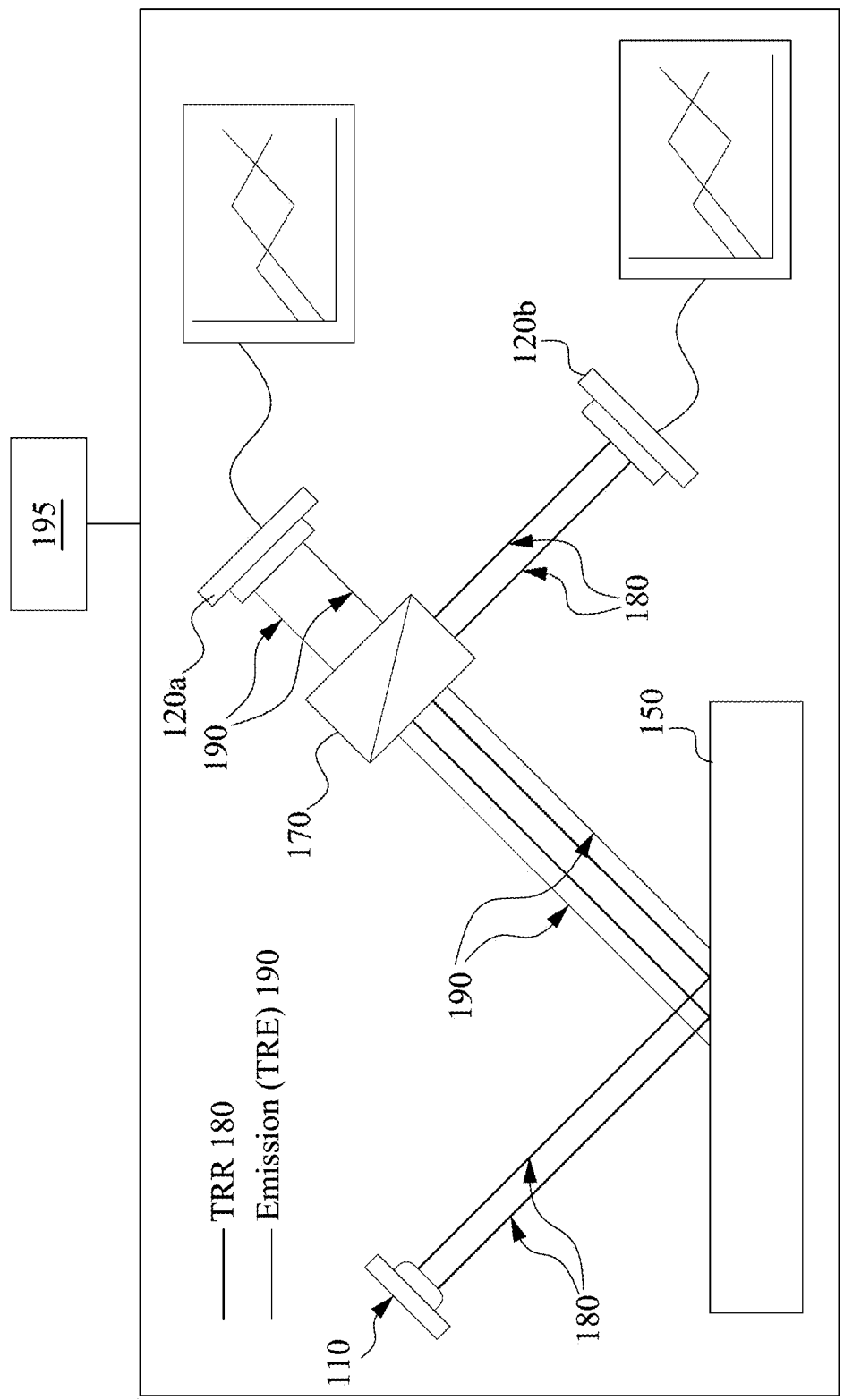
FIG. 1B illustrates a schematic diagram of a temperature evaluating system for a substrate according to further embodiments of the present disclosure.

FIG. 1B illustrates a schematic diagram of a temperature evaluating system for a substrate according to further embodiments of the present disclosure.

For example, FIG. 1B illustrates the light signal propagation of the light 180 emitted from the light emitting source 110. The light 180 is reflected from the surface of the substrate 150 and received at a receiver 170 and then to a detector 120b configured to receive light 180 from the light emitting source 110. In some embodiments, the receiver 170 receives the light 180 and reflects to the appropriate detector 120b for analyzing the light 180 (which includes the time resolved reflectivity (TRR) signals). An emission signals 190 reflected from the surface of the substrate 150 is also received at the receiver 170 and then to a detector 120a configured to receive emission signals 190 from the surface of the substrate 150. The emission signals 190 include the time resolved emission (TRE) signals.

In some embodiments, the temperature evaluating system is operatively coupled to a processor 195 (or controller 195). The processor 195 may include any electrical circuitry, features, components, an assembly of electronic components or the like configured to perform the various operations of the temperature evaluating system as described herein. In some embodiments, the processor 195 may be included in or otherwise implemented by processing circuitry such as a microprocessor, microcontroller, integrated circuit, chip, microchip or the like.

Figure 2A:
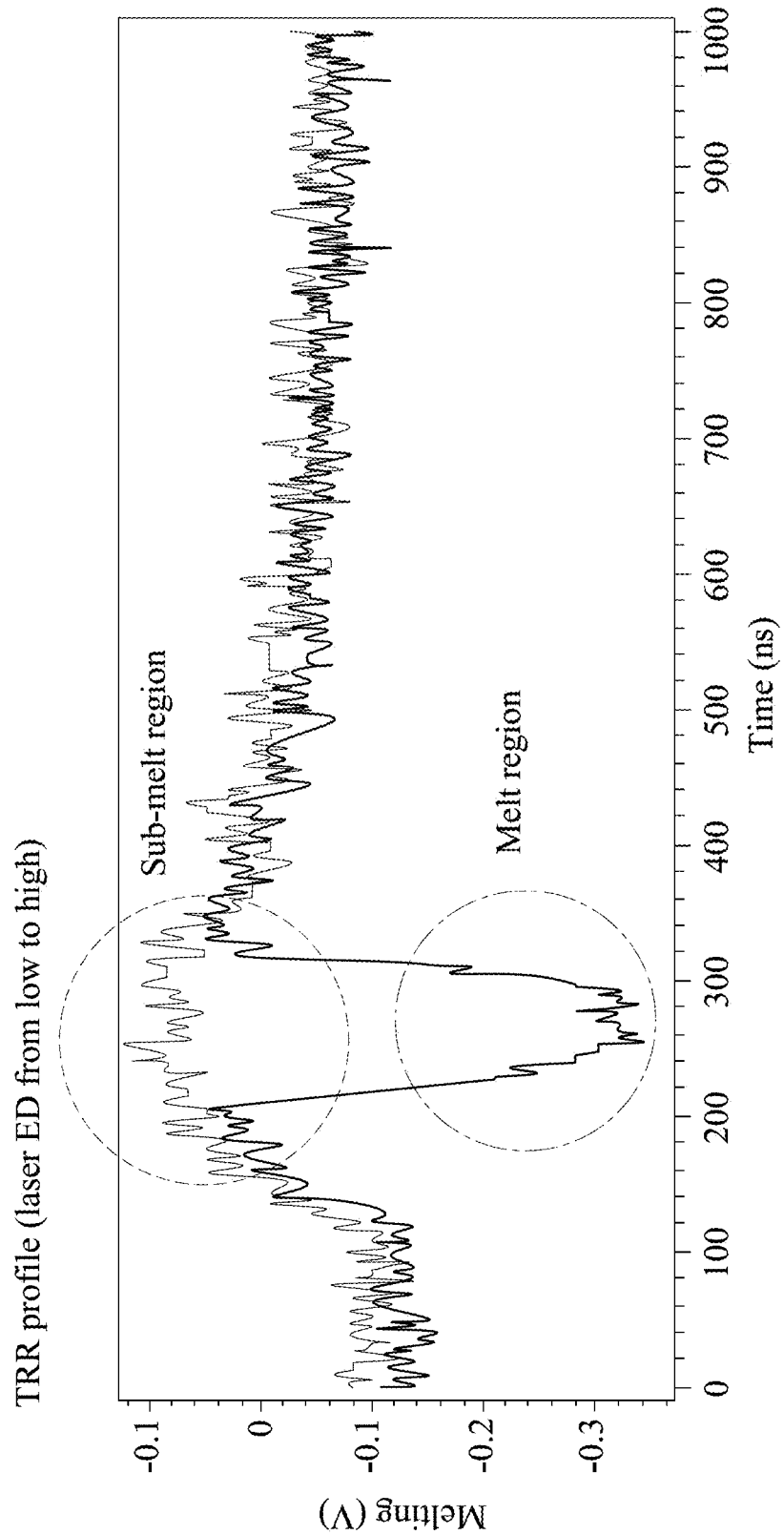
FIG. 2A illustrates a graph showing the fluctuation of the time resolved reflectivity signals at a melt region and a sub-melt region.

FIG. 2A illustrates a graph showing the fluctuation of the time resolved reflectivity signals at a melt region and a sub-melt region. As shown, the x-axis indicates the time in nanoseconds (ns) and the y-axis indicates voltages indicative of energy densities (e.g., melting voltages). The time resolved reflectivity (TRR) signals are shown to increase as the heating source 140 applied against the substrate 150 increases the temperature of the substrate 150. The melt region is indicated by a circle on the bottom of the graph (close to the x-axis) and the sub-melt region is indicated by a circle on the top of the graph. In the melt region, however, the time resolved reflectivity signals drastically drop at melting voltages. This is at least partially due to the fact that a structure (e.g., a component, a metal wiring, or the like) on the substrate 150 or the substrate 150 itself has reached the melting point and melted. For example, when the light signals (e.g., laser or laser pulse) hit the substrate, the reflectivity changes. While the sub melt region is still at a solid phase, once it reaches the melt region, it will reach a liquid phase (will have more like a mirror like effect with respect to reflectivity) and the reflectivity will change. That is, when there is a phase transition, for example from a solid phase to a liquid phase, the time resolved reflectivity signals change. When the time resolved reflectivity signals are used to detect whether there was a phase transition during the anneal process, only utilizing the time resolved reflectivity signals creates problems as shown in FIG. 2A.

Figure 2B:
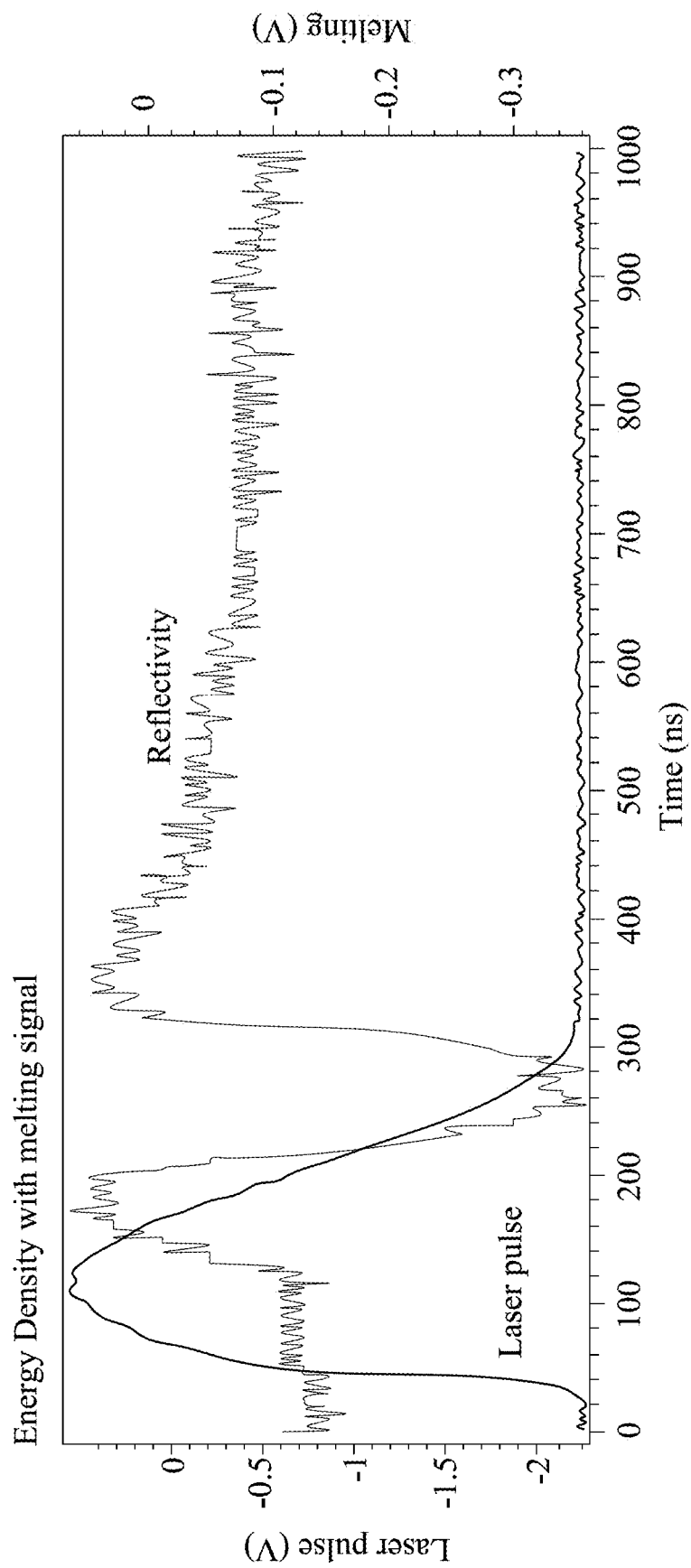
FIG. 2B illustrates a graph showing time resolved reflectivity for different phase transition in terms of energy density with melting signal.

Accordingly, the detection of the precise time when the structures on the substrate 150 melted was not possible to obtain using only the time resolved reflectivity signals. Namely, the detection of when the structures on the substrate 150 melted could be identified only after the structure on the substrate 150 has already started to melt or already melted and not prior to the meltdown. FIG. 2B also illustrates a similar problem that stems from only utilizing the time resolved reflectivity signals to evaluate the temperature of the surface of the substrate 150.

FIG. 2B illustrates a graph showing time resolved reflectivity for different phase transitions in terms of energy density with melting signal. As shown, the x-axis indicates the time in nanoseconds (ns) and the y-axis on the left indicates voltages of the laser pulse applied from the heating source 140 and the y-axis on the right indicates voltages (e.g., melting voltages) of the time resolved reflectivity signals. The time resolved reflectivity (TRR) signals are shown to increase shortly after the laser pulse is applied against the substrate 150. For example, the peak of the time resolved reflectivity signals (at approximately around 180 ns) comes shortly after the peak of the laser pulse voltages (at approximately around 120 ns). However, once the temperature reaches the melting point, the voltages of the time resolved reflectivity signals plummets. Similarly, as explained in connection with FIG. 2A, this is at least partially due to the fact that a structure on the substrate 150 or the substrate 150 itself has reached the melting point and melted and a phase transition has occurred (for example, from a solid phase to a liquid phase). FIG. 2B, similar to FIG. 2A, illustrates a problem of only utilizing the time resolved reflectivity signals to evaluate the temperature of the surface of the substrate 150.

As described above, reflectivity is sensitive to phase change (e.g., changes from solid phase to liquid phase, or the like). That is, the sudden change in reflectivity implies that the substrate 150 is starting to melt and at this point, the temperature may be very close to the melting point. In accordance with some embodiments described herein, by changing the polarization of the light emitting source 110 through the polarizer 130, a more sensitive TRR profile (or reflectivity signal profile) is obtained. This will be further detailed below. For example, the S-polarization has a significantly higher reflectivity output (or signal to noise ratio) compared to the P-polarization. While using the P-polarization still enables the temperature evaluating apparatus to detect the signal, the detected signal here is either weak or unclear. Accordingly, in one or more embodiments, the S-polarization is used to detect the reflectivity profile. This will be further described in connection with FIGS. 3A, and 3B.

Figure 3A:
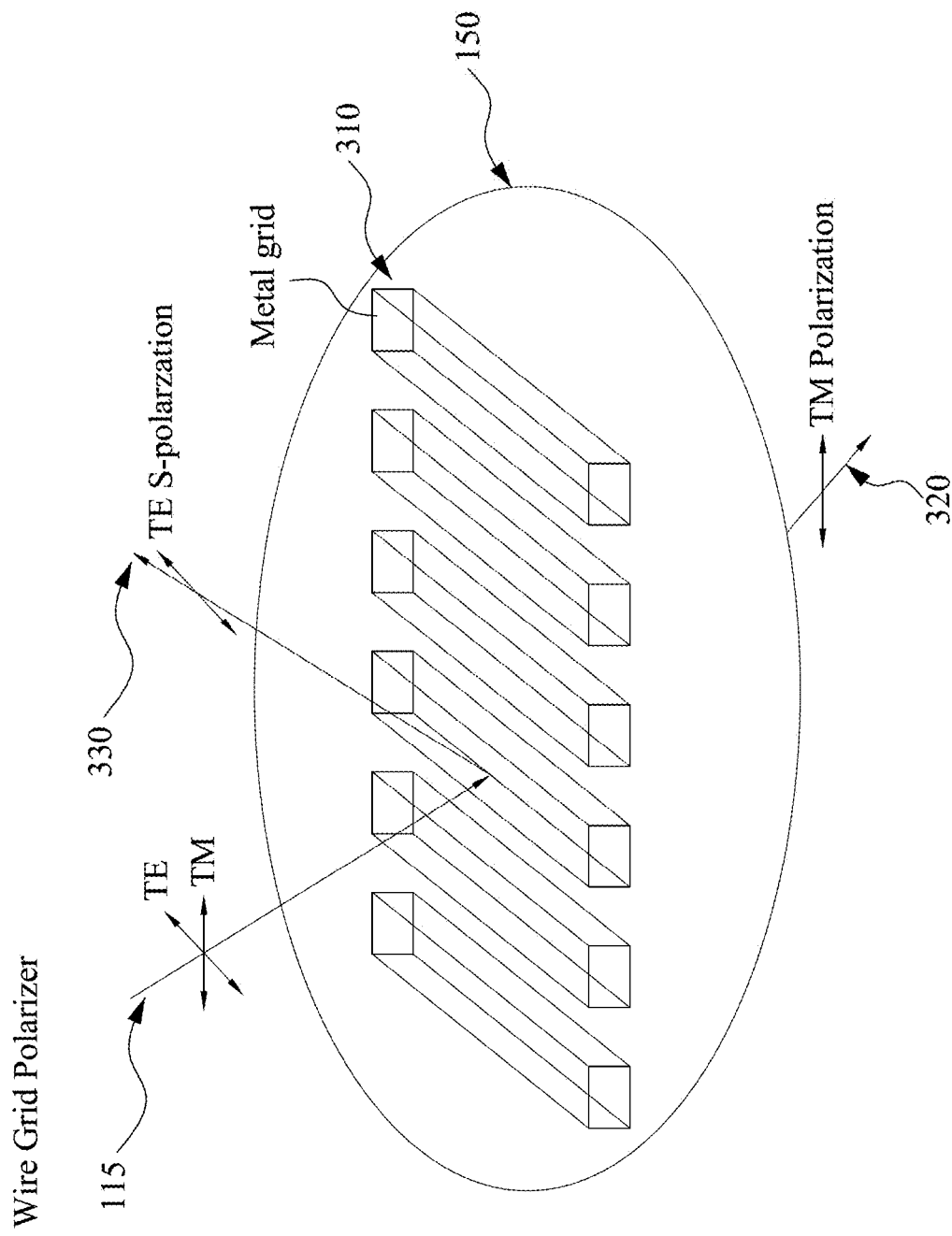
FIG. 3A illustrates a reflection and penetration of light signals at a surface of a substrate having thereon metallic structures.
Figure 3B:
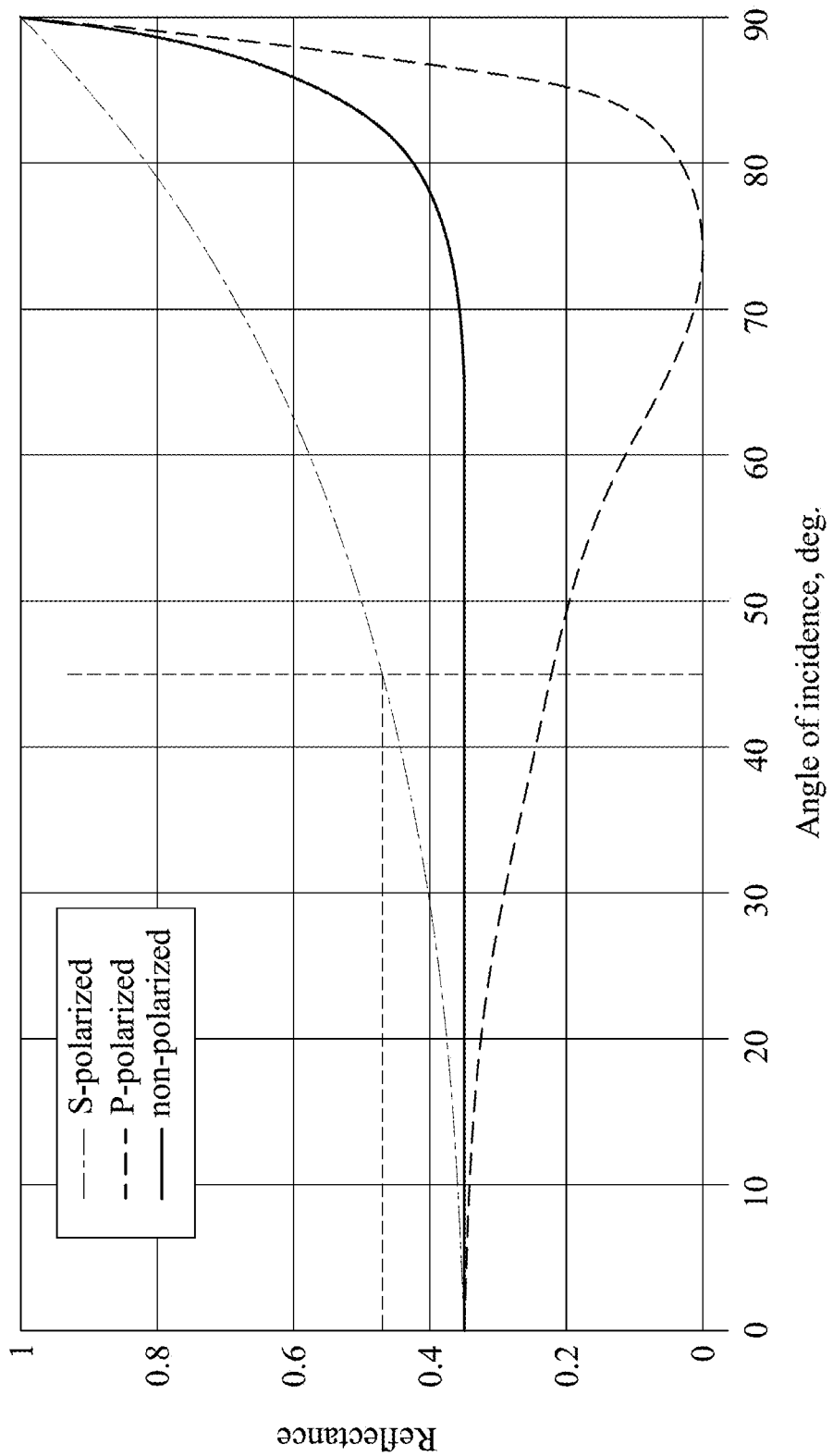
FIG. 3B illustrates a reflectance rate of TE waves, TM waves based on an angle of incidence θ as provided from RefractiveIndex.info.

FIG. 3A illustrates a reflection and penetration of light signals 115 at a surface of a substrate 150 having thereon metallic structures 310. The coordinates may be expressed in Cartesian coordinates as well. FIG. 3B illustrates a reflectance rate of TE waves, TM waves based on an angle of incidence θ as provided from RefractiveIndex.info. FIG. 4 illustrates a graph showing a signal to noise ratio of a time resolved reflectivity signal for TE waves and TM waves. In one or more embodiments, the substrate 150 may have various metallic structure 310 or patterned structures mounted on the substrate 150. The metallic structure 310 includes components, wirings, or the like. For example, the metallic structure 310 includes metal wire grids.

Referring to FIG. 3A, the light signals 115 from the light emitting source 110 are propagated towards the surface of the substrate 150. When the light signals 115 including the TE waves and the TM waves contact the metallic structures 310 on the substrate 150, a portion of the light signals (e.g., TM waves 320) penetrates through (or transmits through) the metallic structures 310 and the substrate 150. The TE waves 330 are reflected from the metallic structure 310.

FIG. 3B illustrates a reflectance rate of TE waves, TM waves, an non-polarized waves. As shown, as the angle of incidence θ varies from 0 degrees to 90 degrees, the reflectance rate of TM waves are maintained below 0.4 unless the light signals are applied at an incident angle of 90 degrees. However, for TE waves, the reflectance rate are generally between 0.38 and 1 from 0 degrees to 90 degrees incident angle. Further, it shows that using a polarizer 130 may produce light signals with higher reflectivity. Accordingly, the temperature evaluating apparatus may control the reflectivity based at least upon the polarization of the light signals, angle θ, angle ϕ, and wavelength. Further factors may be considered beside the aforementioned components to improve the signal to noise ratio at the detector's end.

As shown in FIG. 4 which indicates time (in nanoseconds) in the x-axis and outputted reflectivity in voltages in the y-axis, the signal to noise ratio is better for the TE waves 330 (see S-polarization). This is partially because most of the TM waves 320 (see P-polarization) penetrate through the substrate 150 and are not reflected from the surface of the metallic structure 310 or the substrate 150 to be received at the detector 120. TM waves 320 which have P-polarization have restricted movement of electrons perpendicular to the metallic structures 310 (e.g., metal wires). This causes the TM waves 320 to have a low reflection (e.g., the TM waves 320 transmit through the substrate 150) which in turn causes low sensitivity for detection. On the other hand, the TE waves 330 are better reflected from the surface of the metallic structure 310 or the substrate 150 than the TM waves 320, and are received at a relatively higher ratio at the detector 120 than the TM waves 320.

Accordingly, in one or more embodiments, it is beneficial to utilize the polarizer 130 (as shown in FIG. 1A) such that the light signals 115 emitted from the light emitting source 110 are polarized to produce TE waves 330 as TE waves 330 show better signal to noise ratio compared to TM waves 320 at the detector's end. That is, the polarizer 130 enhances the reflectivity signal which in turn returns better signal to noise ratio.

In further embodiments, the reflectivity signals 127 may be received in real-time during, for example, an anneal period (if the current process is a laser anneal process). For example, the reflectivity signals 127 can be collected in multiple data points where one data point has a 20 ns interval. As shown in FIG. 4, the anneal dwell time appears to be approximately 100 ns. That is, the reflectivity signals 127 for the S-polarization changes roughly from 250 ns to 350 ns. Since the change in the reflectivity signals 127 lasts for about 100 ns (i.e., anneal dwell time), in one embodiment, the reflectivity signals 127 may be detected using the detector 120 every 20 ns. However, other periodic or non-periodic detection with various interval times may be utilized.

Figure 5:
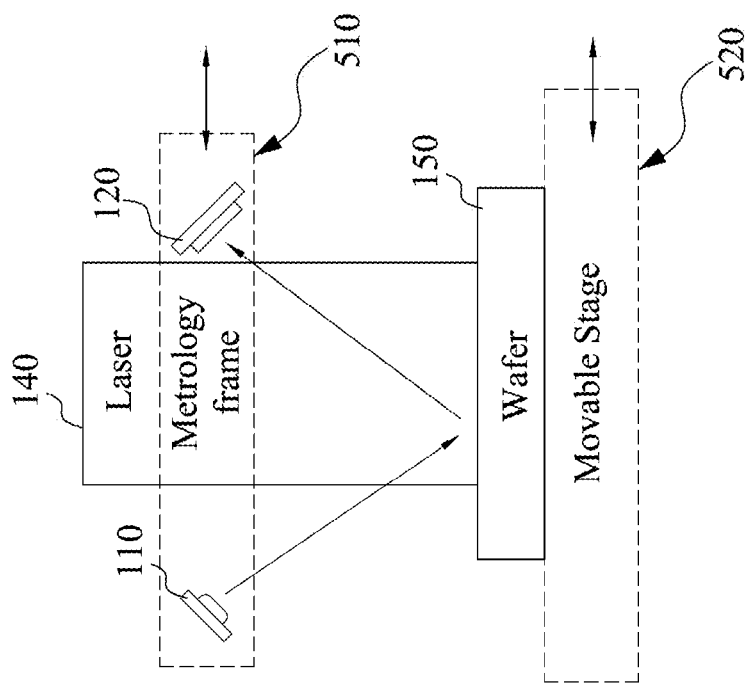
FIG. 5 illustrates a schematic diagram showing a first movable device and a second movable device according to one or more embodiments of the present disclosure.

FIG. 5 illustrates a schematic diagram showing a first movable device and a second movable device according to one or more embodiments of the present disclosure. The first moveable device 510 is connected to the light emitting source 110 and the detector 120. In operation, the first moveable device 510 moves the light emitting source 110 and the detector 120 with respect to the substrate 150. In one or more embodiments, the first moveable device 510 has at least two degrees of freedom of movements (e.g., two degrees, three degrees, and so forth). The second movable device 520 is opposite the first moveable device 510 and the substrate 150 is mounted on the second movable device 520. The second movable device 520 moves concurrently with the substrate 150 on top, and moves with respect to the light emitting source 110 and the detector 120. In one or more embodiments, the second moveable device 520 has at least two degrees of freedom of movements (e.g., two degrees, three degrees, and so forth). In one or more embodiments, the spot where the light emitting source 110 emits light signals 115 may be changed to mechanically offset the location where the laser is applied using the heating source 140 during, for example, an anneal process. To this end, the first moveable device 510 (e.g., a movable frame, a movable metrology frame, or a stage for metrology frame including the light emitting source 110 and the detector 120) is capable of moving the position and location of the light emitting source 110 and may have a resolution that is below in the order of mm (micrometers). Similarly, a stage of the substrate resolution is beneficial to be below the order of micrometers. The first moveable device 510 having thereon the light emitting source 110 and the detector 120 and the second moveable device 520 having thereon the substrate 150 may be used as an in situ method for monitoring temperature during the laser anneal process. In one or more embodiments, it is beneficial for the second moveable device 520 (e.g., the stage of the substrate) to be more precise than the first moveable device 510 (e.g., the monitor stage). In some embodiments, the light emitting source 110 and the detector 120 may be mounted on the same plane of the frame (e.g., stage for metrology frame).

Figure 6A:
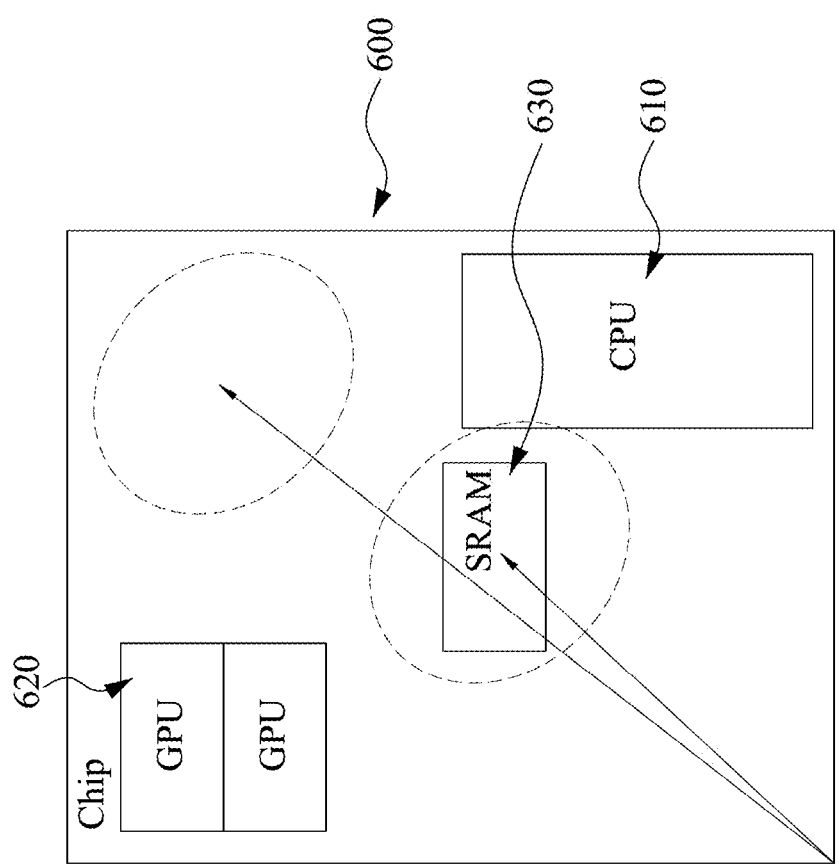
FIG. 6A is a layout of an example chip having thereon various components.
Figure 6B:
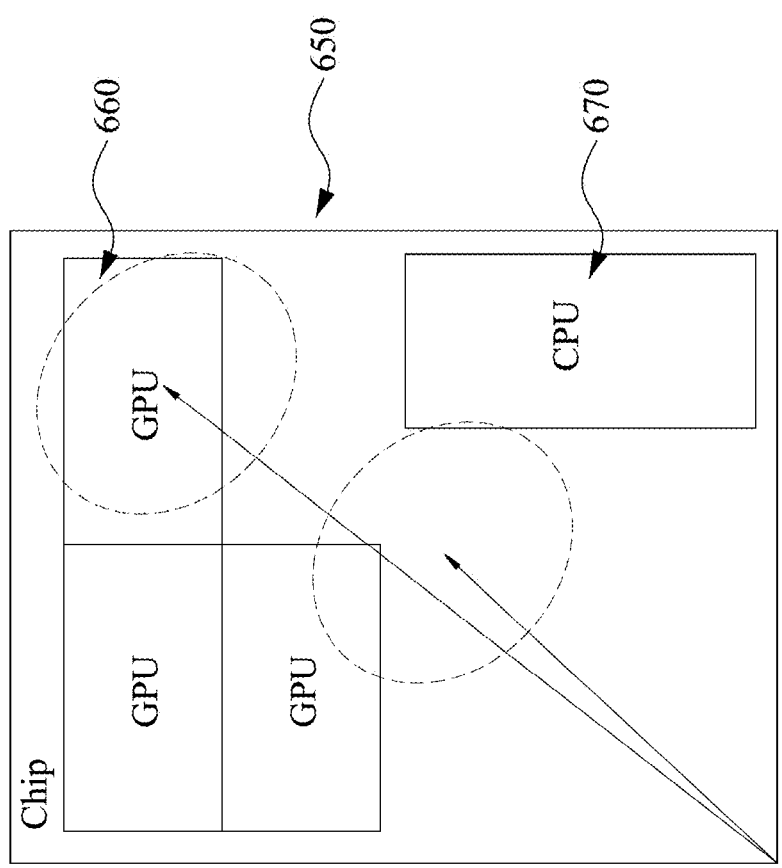
FIG. 6B is a layout of another example chip having thereon various components.

FIG. 6A is a layout of an example chip 600 having thereon various components. As shown, central processing units (CPUs) 610, graphics processing units (GPUs) 620, and static random-access memories (SRAMs) 630 are arranged at various locations within the chip 600. A monitoring spot can be moved to monitor the critical area where the critical components (e.g., CPU, GPU, SRAM, or the like) are located. In some embodiments, the monitor spot is fixed. However, a chip may have the CPUs, GPUs, SRAMs, or other critical components at various locations within the chip. For example, an SRAM may be located in the middle of the chip (see FIG. 6A). A GPU, on the other hand, may be located in the top left corner of the chip. In these cases, the monitor spot needs to be shifted to the top right portion of the chip. And for other type of chips, the SRAM may not be necessarily located in the middle of the chip and the GPU may not be necessarily located in the top right corner of the chip. This is shown in FIG. 6B. Accordingly, in one or more embodiments, a movable stage (e.g., a moveable device) can move in various directions to adjust the monitor spot.

SRAM, for example, is a chip that has a high density. The SRAM as well as the above mentioned components are critical components of the chip 600 which require monitoring during the processing of the chip 600 (e.g., laser anneal process). FIG. 6B is a layout of another example chip 650 having thereon various components. Contrary to the chip 600 in FIG. 6A, the locations and arrangements of the various components are different from that shown in the chip 650 of FIG. 6B. For instance, while the GPUs 620 were located mostly around the upper left corner of the chip 600, the GPUs 660 of the chip 650 are located on the upper right corner or the upper central region. For example, while the CPUs 610 were located above the bottom right corner of the chip 600, the CPUs 670 of the chip 650 are located on the bottom right corner. Further, the size, the number, and the precise location of the CPUs/GPUs of the second chip 650 is different from the first chip 600. That is, every chip will mount circuit components at different locations based on various design requirements. Further, some components may not be present. For example, there are no SRAMs shown in the chip 650.

Accordingly, because the location of the critical components such as CPUs, GPUs, SRAMs, or the like, differs from every chip, the first and second movable devices 510, 520 can change the location of where the light signals 115 are emitted towards to offset for the different location of the critical components within each chip.

Referring to FIG. 5, in some embodiments, the position of the heating source 140 is fixed. That is, for example, it is beneficial for the probe laser 110 to move as the laser shot (from the heating source 140) against the substrate 150 is generally fixed. Thus, the first moveable device 510 can move around, for example, in a direction shown in the arrow to locate the critical components for each chip. Additionally or alternatively, the second moveable device 520 may move around in a direction shown in the arrow to locate the critical components during the laser anneal process. In some embodiments, both the first moveable device 510 and the second moveable device 520 may move together to locate the position of the critical components for each chip. In one or more embodiments, the light emitting source 110 and the detector 120 may be fixated within the first moveable device 510 at a certain location and may move together with the first moveable device 510 to adjust the monitor spot of the substrate 150. In further embodiments, the second moveable device 520 that adjusts the position of the substrate 150 and the first moveable device 510 that adjusts the position of the light emitting source 110 and the detector 120 can be provided together. In these embodiments, the offset distance (e.g., a distance that needs to be adjusted to monitor the temperature of various critical components such as the CPU, GPU, SRAM, etc., within select locations in a chip) may be reduced or minimized.

Figure 7:
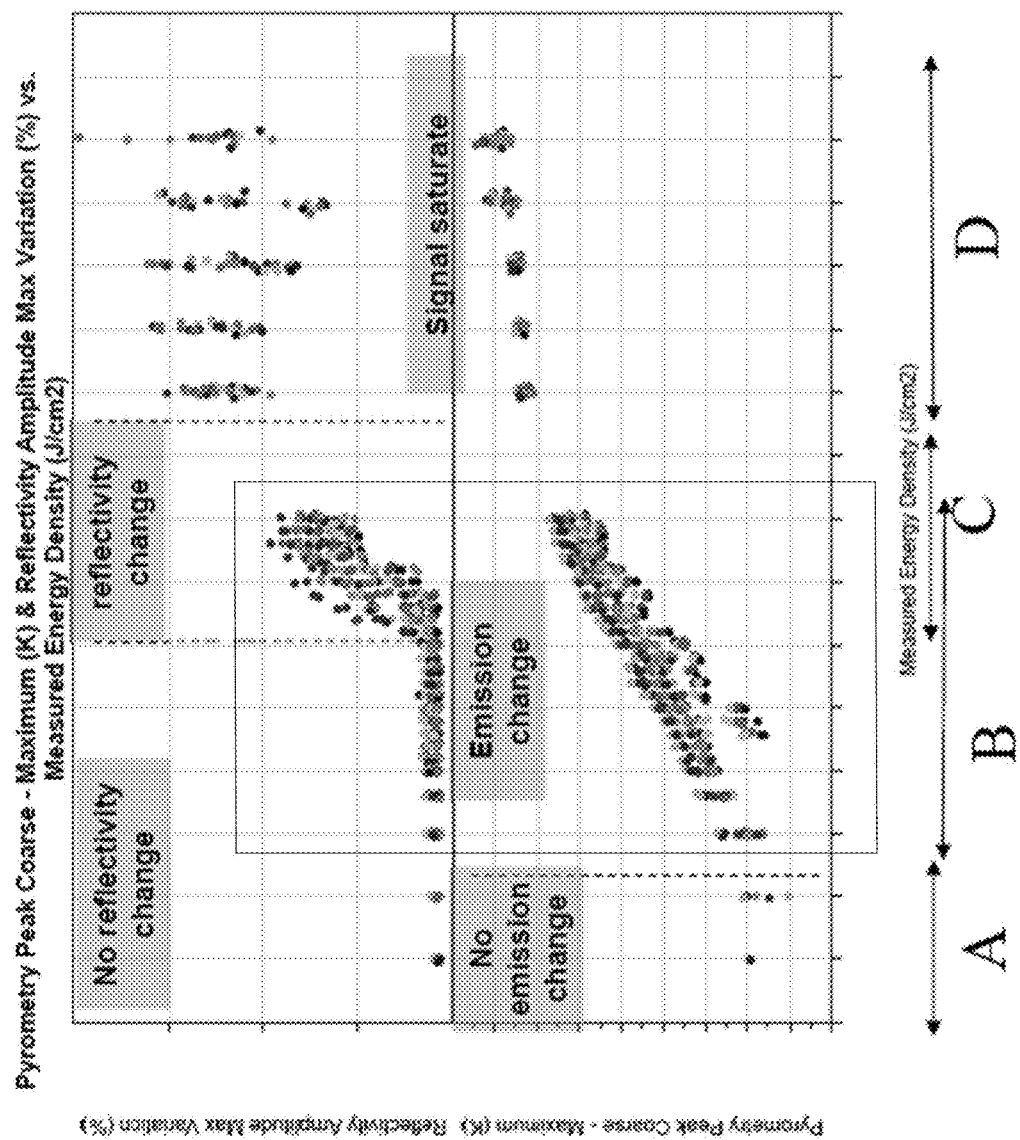
FIG. 7 is a graph illustrating the range of energy density capable of being detected using a combination of emission signals and reflectivity signals according to temperature measuring apparatus of the present disclosure.

FIG. 7 is a graph illustrating the range of energy density capable of being detected using a combination of emission signals and reflectivity signals according to temperature measuring apparatus of the present disclosure. As shown, FIG. 7 describes that by detecting energy density through emission signals at the detector 120, it is possible to detect the change of the temperature of the surface of the substrate 150 when the energy density of the substrate 150 starting at the B interval (the B interval includes the section where emission signal changes). That is, the detector 120 measuring the energy density of the substrate 150 can detect energy densities within the B interval. In the A interval (the A interval includes the section where there is no change in emission signals), the minimal or no reflectivity changes or emission changes is detected. In the D interval (the D interval includes the section where both the reflectivity signal and the emission signal are saturated), the reflectivity and emission signals are saturated.

The detector 120 can start detecting the energy density of the substrate 150 through the reflectivity signals at the C interval (the C interval includes the section where reflectivity signal changes). Namely, by using the emission signals, the detector 120 can start detecting lower energy densities compared to using reflectivity signals. As explained above, using only the reflectivity signals caused the inaccurate timing of noticing temperature changes of the substrate. The method of using the emission signals also shows a tight threshold value which is also an improvement compared to the method of using the reflectivity signals. The threshold value is important in that it assists in identifying the condition of the various processes (e.g., anneal process, thermal process, or the like). For example, a threshold point for process condition for an anneal process may be identified.

Figure 8A:
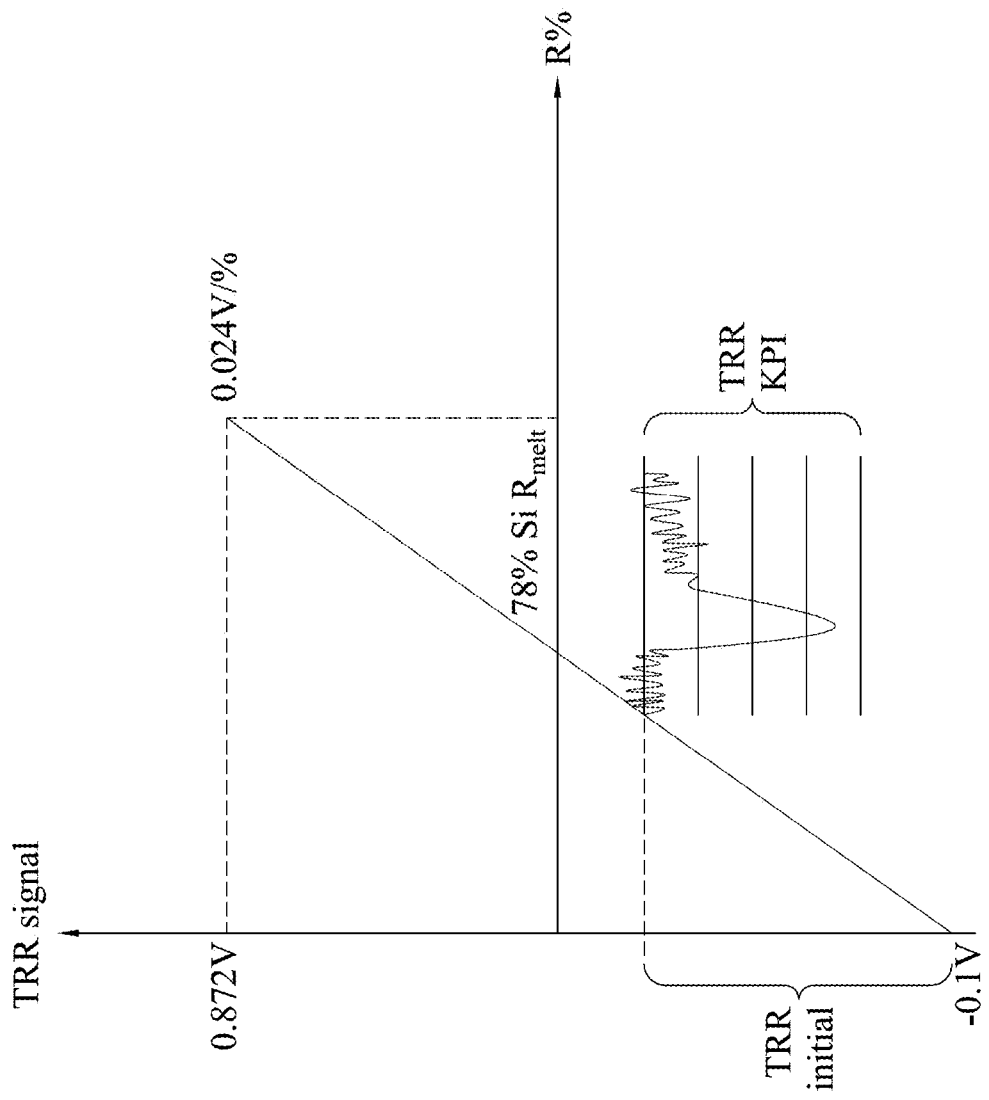
FIGS. 8A and 8B are graphs showing that a light emitting source may be calibrated to improve reflectivity according to the present disclosure.
Figure 8B:
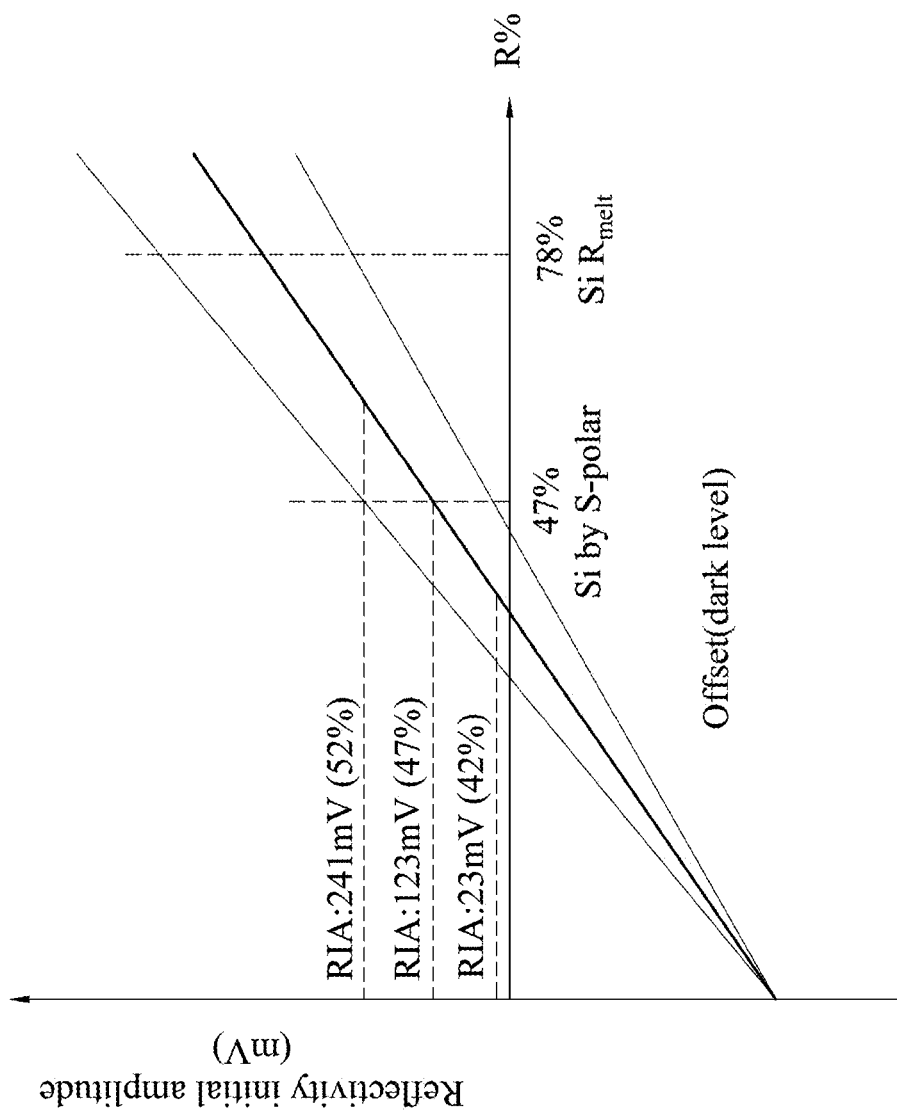

FIGS. 8A and 8B are graphs showing that a light emitting source may be calibrated to improve reflectivity according to the present disclosure.

FIGS. 8A and 8B show the light emitting source 110, for example the probe laser, being calibrated under various conditions. Here, in FIG. 8A, the x-axis is reflectivity (%)

and the y-axis is the reflectivity signal which varies from −1.0V to 0.872V. As indicated by the graph, the reflectivity at melting temperature for Si (e.g., a bare Si wafer) is about 78%. However, the reflectivity for Si at room temperature is 47%. Accordingly, under specific conditions including ambient temperatures, the quality of the light emitting source 110 may be improved.

In FIG. 8B, the x-axis is reflectivity (%) and the y-axis is the reflectivity initial amplitude (mV). By calibrating the light emitting source 110, it is possible to define the dark level (e.g., offset) and the reflectivity of various materials of the substrate. In this case, FIG. 8B shows the reflectivity changes of a bare Si. Based on the variations of the reflectivity of the Si, it is possible to determine the conditions including the threshold points for the thermal process (e.g., thermal anneal process).

Figure 9:
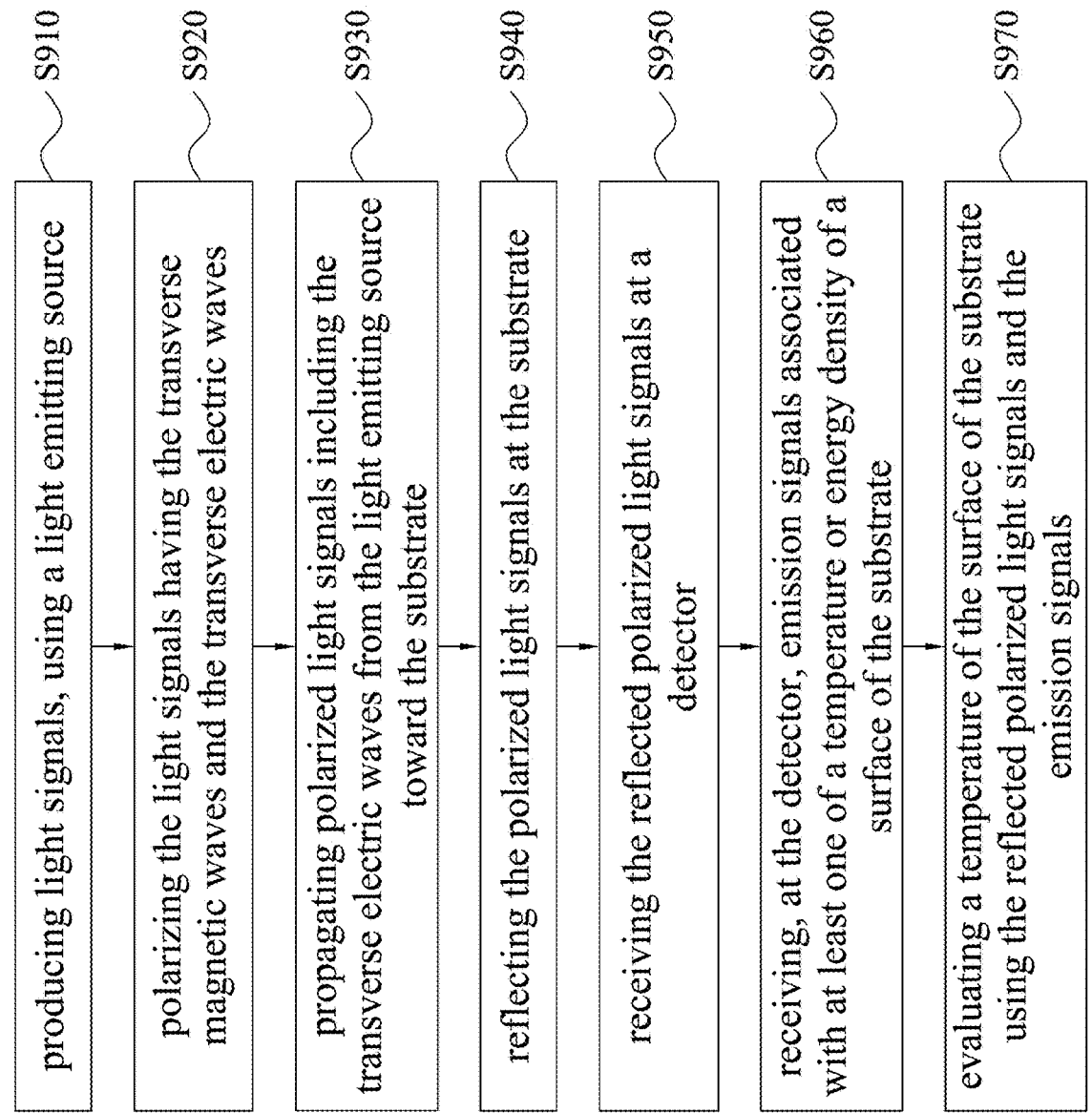
FIG. 9 is a method of evaluating a temperature of a substrate according to some embodiments of the present disclosure.

FIG. 9 is a method 900 of evaluating a temperature of a substrate according to some embodiments of the present disclosure. The method includes producing light signals, using a light emitting source (at step S910). The light signals have transverse magnetic waves and transverse electric waves. The method further includes polarizing the light signals having the transverse magnetic waves and the transverse electric waves (at step S920). The method further includes propagating polarized light signals including the transverse electric waves from the light emitting source toward the substrate (at step S930). The method further includes reflecting the polarized light signals at the substrate (at step S940). The method further includes receiving the reflected polarized light signals at a detector (at step S950). The method further includes receiving, at the detector, emission signals associated with at least one of a temperature or energy density of a surface of the substrate (at step S960). The method further includes evaluating a temperature of the surface of the substrate using the reflected polarized light signals and the emission signals (at step S970).

In one or more embodiments, an in situ method to monitor laser anneal process temperature is described. The in situ method to monitor laser anneal process involves using a polarized probe laser and an emission detector. The emission detector is configured to detect the reflectivity signals and the emission signals. The two signals received at the emission detector may be used to compute temperature of various structures on the substrate.

Further aspects of the present disclosure are provided to improve sensitive in situ monitoring of the various thermal processes.

One embodiment of the present disclosure provides a temperature evaluating system for a substrate. The system includes a light emitting source, which, in operation, produces light signals. The system further includes a polarizer, which, in operation, receives transverse magnetic waves and transverse electric waves from the light emitting source and transmits polarized light signals toward the substrate at a selected incident angle. Here, the polarized light signals include the transverse electric waves of the light signals. The system further includes a detector, which, in operation receives reflectivity signals that includes the transverse electric waves of the light signals reflected from a surface of the substrate. The detector, in operation, further receives emission signals emitted from the surface of the substrate. The emission signals vary with at least one of a temperature or energy density of the surface of the substrate.

Yet another embodiment of the present disclosure provides a temperature measuring apparatus for a substrate. The apparatus includes a light emitting source, which, in operation, produces light signals. The apparatus further includes a polarizer configured to receive the light signals including the transverse magnetic waves and the transverse electric waves from the light emitting source, and polarize the received light signals and transmit polarized light signals toward a substrate. The polarized light signals include the transverse electric waves of the light signals. The apparatus further includes a detector, which, in operation receives reflectivity signals that include the transverse electric waves of the light signals reflected from a surface of the substrate. The detector, in operation, further receives emission signals emitted from the surface of the substrate. The emission signals are representative of at least one of a temperature or energy density of the surface of the substrate. The apparatus further includes one or both of a first movable stage and a second movable stage. The first movable stage has mounted thereon the light emitting source and the detector. The first movable stage is configured to move the light emitting source and the detector. The second movable stage supports the substrate. The second movable stage is configured to move the substrate.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A temperature evaluating system for a substrate, comprising:
   a light emitting source, which, in operation, produces light signals, the light signals having transverse magnetic waves and transverse electric waves;
   a polarizer, which, in operation, receives transverse magnetic waves and transverse electric waves from the light emitting source and transmits polarized light signals toward a surface of the substrate at a selected incident angle, wherein the polarized light signals include the transverse electric waves of the light signals, the selected incident angle with respect to the surface of the substrate being between about 10° to 80°;
   a detector, which, in operation:
      receives reflectivity signals that includes the transverse electric waves of the light signals reflected from the surface of the substrate; and
      receives emission signals emitted from the surface of the substrate, wherein the emission signals vary with at least one of a temperature or energy density of the surface of the substrate.

2. The temperature evaluating system of claim 1, further comprising a laser to heat the surface of the substrate, the laser positioned above the substrate, wherein the laser operates at a range of wavelengths between about 300 nm to 320 nm.

3. The temperature evaluating system of claim 1, wherein the light emitting source includes a probe laser.

4. The temperature evaluating system of claim 1, further comprising a processor, which, in operation, determines the temperature of the surface of the substrate based on the following equation:

$$T = \frac{A}{\ln\left(1 + B \cdot \frac{\varepsilon}{TRE}\right)}$$

wherein T is the temperature of the substrate, A and B are a constant parameter, $\varepsilon$ is emissivity which equals 1−R %, R is the reflectivity signals, and TRE is the emission signals.

5. The temperature evaluating system of claim 4, wherein the detector is configured to receive a range of wavelengths of the emission signals that is between about 1500 nm (nanometer) to 1600 nm, and receive a range of wavelengths of the reflectivity signals that is between about 620 nm to 650 nm.

6. The temperature evaluating system of claim 1, further comprising:
a first movable stage to which the light emitting source and the detector are mounted, the first movable stage being configured to move the light emitting source and the detector with at least two degrees of freedom.

7. The temperature evaluating system of claim 1, further comprising:
a second movable stage for supporting the substrate, the second movable stage configured to move the substrate with at least two degrees of freedom.

8. A temperature measuring apparatus for a substrate, comprising:
a light emitting source, which, in operation, produces light signals, the light signals having transverse magnetic waves and transverse electric waves;
a polarizer configured to receive the light signals including the transverse magnetic waves and the transverse electric waves from the light emitting source, polarize the received light signals and transmit polarized light signals toward a substrate, wherein the polarized light signals include the transverse electric waves of the light signals;
a detector, which, in operation:
receives reflectivity signals that includes the transverse electric waves of the light signals reflected from a surface of the substrate, and
receives emission signals emitted from the surface of the substrate, wherein the emission signals are representative of at least one of a temperature or energy density of the surface of the substrate;
a first movable stage having thereon mounted the light emitting source and the detector, the first movable stage configured to move the light emitting source and the detector; and
a processor configured to process the emission signals and the reflectivity signals,
wherein the processor evaluates the temperature of the surface of the substrate based on the following equation:

$$T = \frac{A}{\ln\left(1 + B \cdot \frac{\varepsilon}{TRE}\right)}$$

wherein T is the temperature of the substrate, A and B are a constant parameter, $\varepsilon$ is emissivity which equals 1−R %, R is the reflectivity signals, and TRE is the emission signals.

9. The temperature measuring apparatus of claim 8, wherein the
processor is further configured to evaluate the temperature of the surface of the substrate.

10. The temperature measuring apparatus of claim 8, wherein the first movable stage is configured to move the light emitting source and the detector with either two degrees of freedom or three degrees of freedom.

11. The temperature measuring apparatus of claim 8, further comprising a second movable stage for supporting the substrate, the second movable stage configured to move the substrate and wherein the second movable stage is configured to move the substrate in a first direction and in a second direction that is transverse to the first direction.

12. A temperature evaluating system, comprising:
a light emitting source configured to produce light signals, the light signals having transverse magnetic waves (TM) and transverse electric waves (TE);
a polarizer configured to polarize the light signals having the transverse waves and transverse electric waves;
a detector configured to:
receive the polarized light signals reflected from a substrate, the reflected polarized light signals being reflected at a surface of the substrate;
receive emission signals associated with at least one of a temperature or energy density of the surface of the substrate; and
one or more processors operatively coupled to the detector, the one or more processors configured to evaluate the temperature of the surface of the substrate using the reflected polarized light signals and the emission signals,
wherein the light emitting source is positioned such that the light signals after being polarized by the polarizer is at an incident angle between about 10° to 80° with respect to the surface of the substrate.

13. The temperature evaluating system of claim 12, wherein the one or more processors are configured to calculate the temperature of the surface of the substrate based on the following equation:

$$T = \frac{A}{\ln\left(1 + B \cdot \frac{\varepsilon}{TRE}\right)}$$

wherein T is the temperature of the substrate, A and B are a constant parameter, $\varepsilon$ is emissivity which equals 1−R %, R is an intensity of the reflected polarized light signals, and TRE is an intensity of the emission signals.

14. The temperature evaluating system of claim 12, wherein receiving emission signals associated with at least one of a temperature or energy density of the surface of the substrate includes,
receiving a range of wavelengths of the emission signals that is broader than a range of wavelengths of the reflected polarized light signals.

15. The temperature evaluating system of claim 14, wherein the range of wavelengths of the emission signals is between about 1500 nm to 1600 nm and the range of wavelengths of the reflected polarized light signals is between about 620 nm to 650 nm.

16. The temperature evaluating system of claim 12, further comprising:
a first movable stage configured to move the light emitting source and the detector with respect to the substrate, wherein the light emitting source and the detector are connected to the first movable stage and the first movable stage has at least two degrees of freedom of movement.

17. The temperature evaluating system of claim 12, further comprising:
a second movable stage configured to support the substrate thereon, the second movable stage further configured to move the substrate with respect to the light emitting source and the detector,
wherein the second movable stage has at least two degrees of freedom of movement.

18. The temperature evaluating system of claim 6, further comprising:
a second movable stage for supporting the substrate, the second movable stage configured to move the substrate with at least two degrees of freedom.

19. The temperature measuring apparatus of claim 8, wherein the detector is configured to receive a range of wavelengths of the emission signals that is between about 1500 nm (nanometer) to 1600 nm, and receive a range of wavelengths of the reflectivity signals that is between about 620 nm to 650 nm.

20. The temperature measuring apparatus of claim 8, wherein the light emitting source is positioned such that the light signals after being polarized by the polarizer is at an incident angle between about 10° to 80° with respect to the surface of the substrate.

\* \* \* \* \*